(12) United States Patent
Liu et al.

(10) Patent No.: US 8,486,673 B2
(45) Date of Patent: Jul. 16, 2013

(54) METHOD FOR PRODUCING 1,3-PROPANEDIOL USING CRUDE GLYCEROL, A BY-PRODUCT FROM BIODIESEL PRODUCTION

(75) Inventors: Dehua Liu, Beijing (CN); Hongjuan Liu, Beijing (CN); Yan Sun, Beijing (CN); Rihui Lin, Beijing (CN); Jian Hao, Beijing (CN)

(73) Assignee: Tsinghua University, Beijing (CN)

( * ) Notice: Subject to any disclaimer, the term of this patent is extended or adjusted under 35 U.S.C. 154(b) by 775 days.

(21) Appl. No.: 11/916,180

(22) PCT Filed: Jun. 1, 2006

(86) PCT No.: PCT/CN2006/001181
§ 371 (c)(1),
(2), (4) Date: May 1, 2009

(87) PCT Pub. No.: WO2006/128381
PCT Pub. Date: Dec. 7, 2006

(65) Prior Publication Data
US 2010/0028965 A1   Feb. 4, 2010

(30) Foreign Application Priority Data
Jun. 3, 2005   (CN) .......................... 2005 1 0011867

(51) Int. Cl.
*C12P 7/18* (2006.01)

(52) U.S. Cl.
USPC .............................. 435/158; 435/41; 435/170

(58) Field of Classification Search
None
See application file for complete search history.

(56) References Cited

U.S. PATENT DOCUMENTS 5,599,689 A   2/1997   Haynie et al.
6,136,576 A   10/2000  Diaz-Torres et al.

OTHER PUBLICATIONS

Papanikolaou et al., Journal of Biotechnology, 2000, vol. 77, p. 191-208.*
Gong et al., Desalination, 2004, vol. 161, p. 169-178.*
Chen et al., Appl Microbiol Biotechnol, 2003, vol. 63, p. 143-146.*
Min Enze, "An exploratory on developing biodiesel refinery based on vegetable oil raw materials in china", ACTA PETROL EISINICA (Petroleum processing section), vol. 21 No. 3, pp. 25-28, Jun. 30, 2005, English Abstract.
Wu Bin, He Bingfang et al, "Fermentative production of 1,3-propanediol from glycerol by clostridium butyricum", vol. 34 No. 1, pp. 21-25, Mar. 2004, English Abstract.
Cheng Keke, Ling Hongzhi et al, "Effect of glucose as cosubstrate on 1,3-propanediol fermentation by Klebsiella pneumoniae", vol. 4 No. 6, pp. 561-565, Dec. 2004, English Abstract.
Kirsten Menzel et al, "Enzymatic evidence for an involvement of pyruvate dehydrogenase in the anaerobic glycerol metabolism of Klebsiella pneumoniae", vol. 56, pp. 135-142, 1997.
Xiang Xiaoli, "Preparations of 1,3-propanediol", vol. 17 no. 7, pp. 22-24, 2003, English Abstract.
Jin Hua, The application of biochemical technology in petroleum and petrochemical fields, vol. 32 No. 5, pp. 443-447, 2003, English Abstract.

* cited by examiner

*Primary Examiner* — Kade Ariani
(74) *Attorney, Agent, or Firm* — Millen, White, Zelano, Branigan, P.C.

(57) ABSTRACT

The invention discloses a method for producing 1,3-propanediol, comprising the steps of: using crude glycerol, a by-product during the biodiesel production, without further treatment, as the substrate for production of 1,3-propanediol; inoculating a 1,3-propanediol-producing strain in a seed medium containing crude glycerol, a by-product from biodiesel production; adding the seed culture into a fermentation medium containing crude glycerol, a by-product from biodiesel production, and fermenting; maintaining pH in a range of 6.8 to 8.0; and in the end of the fermentation, isolating and purifying 1,3-propanediol.

13 Claims, 1 Drawing Sheet

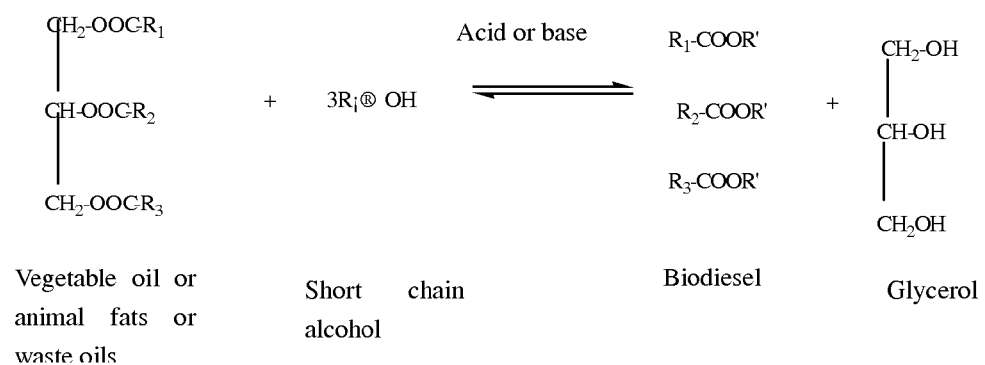

METHOD FOR PRODUCING 1,3-PROPANEDIOL USING CRUDE GLYCEROL, A BY-PRODUCT FROM BIODIESEL PRODUCTION

This application is a U.S. National Stage Application based on International Patent Application No. PCT/CN2006/001181, filed Jun. 1, 2006, which is based on China Application No. 200510011867.8, filed Jun. 3, 2005.

FIELD OF THE INVENTION

The invention relates to biochemical engineering field. Particularly, a method for producing 1,3-propanediol using crude glycerol, a by-product from biodiesel production, is provided.

BACKGROUND OF THE INVENTION

Biodiesel, one of the renewable energy sources, is made from vegetable oils, animal fats or waste oils, such as cooking oils, as shown in FIG. 1.

Biodiesel has been widely used in many countries and regions, such as US, Europe and Japan, as a clean renewable energy. Up to now, biodiesel has not been industrialized in China. The methods for biodiesel production mainly include:

(1) chemical method, which is mainly used in industry at present, wherein the glycerol-group of vegetable oils or animal oils is substituted by low-carbon alcohols such as methanol or ethanol to produce corresponding fatty acid methyl esters or fatty acid ethyl esters by transesterification in the presence of acidic or basic catalysts (Ma F, Hanna M A. Biodiesel production: a review. Bioresource Technology, 1999, 70: 1~15).

(2) biological method, wherein biological enzymes or cells are used to catalyze transesterification reaction and the corresponding fatty acid methyl esters or fatty acid ethyl esters are produced (Ma F, Hanna M A. Biodiesel production: a review. Bioresource Technology, 1999, 70: 1~15).

(3) supercritical method, wherein transesterification reaction is carried out in a supercritical solvent system without any catalysts. (Saka S, Kusdiana D. Biodiesel fuel from rapeseed oil as prepared in supercritical methanol. Fuel, 2001, 80 (2): 225~231; Kusdiana D, Saka S. Kinetics of transesterification in rapeseed oil to biodiesel fuel as treated in supercritical methanol. Fuel, 2001, 80 (5): 693~698; Miao Xiao-ling, Wu Qing-yu, Exploitation of biomass renewable energy sources of microalgae. Renewable Energy, 2003, No. 3: 13~16).

During the production of biodiesel using above methods, a by-product, glycerol, is obtained. With the biodiesel production increasingly growing up, the glycerol production is increased correspondingly. How to efficiently utilize the glycerol, a by-product from biodiesel production, becomes a common problem for large amount of biodiesel production.

As an organic solvent, 1,3-propanediol (PDO) is an important chemical raw material in industries, such as in the areas of printing ink, dying, coating, lubricant, and anti-freeze agent. 1,3-propanediol is mainly used as monomer in the synthesis of polyesters and polyurethanes, especially in the synthesis of poly(trimethylene terephthalate) (PTT) by polymerization of terephthalic acid and 1,3-propanediol, exhibiting an advantageous characteristic over the traditional polymers obtained by the polymerization of monomer 1,2-propanediol, butanediol, or ethanediol. Tens of million tons of poly(ethylene terephthalate) (PET) are consumed all over the world yearly. PTT has comparable chemical stability and biological degradability with those of PET, but is more advantageous in terms of pollution resistance, ductility and elastic resilience as well as ultraviolet resistance. In addition, PTT fibers have the advantages of wear-resistance, low water absorbability and weak static, and are able to compete with nylon in carpet industry. It also can be used in non-woven fabrics, engineering plastics, clothing, household ornaments, paddings and fabrics. PTT was evaluated as one of 1998's Six New Petrochemical Products in the US and considered as an alternative of PET.

The superior performance and commercial potential of PTT has been recognized as early as 50 years ago. It is very difficult to produce PTT in an industrial scale due to the difficulty and high cost of 1,3-propanediol production. Currently, only DuPont and Shell can synthesize 1,3-propanediol for the production of PTT in large scale, employing oxane or propene as raw materials. The disadvantages of chemical method include, for example, more by-products, poor selectivity, high temperature and pressure required for operation, excessive investment in equipment, non-renewable raw material, and inflammable, explosive or extremely toxicity of oxane and acrolein, an intermediate of another synthesis pathway. The production of 1,3-propanediol by fermentation has become the focus of attention in recent years because of its high selectivity and mild operation conditions. Now, the main routes of the production of 1,3-propanediol from glycerol by fermentation include:

1) conversion of glycerol to 1,3-propanediol by fermentation under anaerobic condition using Enterobacteria (U.S. Pat. No. 5,254,467, EP0373230 A1).

2) production of 1,3-propanediol by fermentation under anaerobic condition using anaerobic bacteria such as *Klebsiella* (Ruch et al. Regulation of glycerol catabolism in *Klebsiella aerogenes*. J. Bacteriol. 1974, 119(1):50~56; Streekstra et al. Overflow metabolism during anaeric growth of *Klebsiella pneumoniae* NCTC418 on glycerol and dihydroxyacetone in chemostat culture. Arch Microbiol. 1987, 147:268~275; Zeng et al. Pathway analysis of glycerol fermentation by *Klebsiella pneumoniae*: Regulation of reducing equivalent balance and product formation. Enzyme Microbiol Technol. 1993, 15:770~779).

3) production of 1,3-propanediol by fermentation under microaerobic condition using *Klebsiella* (Wang Jian-feng et al, Study on microaerobic conversion of glycerol to 1,3-propanediol by *Klebsielle pneumoniae*. Modern Chemical Industry, 2001, 21 (5): 28-31. Xiu Zhi-long et al, A method of production of 1,3-propanediol by fermentation using microbes under microaerobic condition, Chinese Patent Publication No.: CN1348007).

4) production of 1,3-propanediol and 2,3-butanediol by fermentation under anaerobic condition using *Klebsiella* (Biebl et al. Fermentation of glycerol to 1,3-propanediol and 2,3-butanediol. Appl Microbiol Biotechnol, 1998, 50:24-29).

The raw materials used in above routes are all from the reagent glycerol or the fermentation broth containing glycerol. Up to now, there is no report on the production of 1,3-propanediol by fermentation of crude glycerol, a by-product from biodiesel production. Xiu Zhi-long et al (Xiu Zhi-long et al, A linked method of production of biodiesel and 1,3-propanediol, Chinese Patent Publication No.: CN1648207A) proposed that glycerol could be isolated by filtering the by-products from biodiesel production through membrane and used to produce 1,3-propanediol by fermentation, but this method is hard to carry out due to the cost of membrane filter and the difficulties of cleaning and regenerating the membranes. Moreover it is very difficult to perform both processes simultaneously, especially production in a large scale.

SUMMARY OF THE INVENTION

The present invention provides a method of 1,3-propanediol production by direct use of crude glycerol, a by-product from biodiesel production, saving the expenditure of glycerol isolation and purification, and reducing the cost effectively. The method is useful in the integrated production of biodiesel and 1,3-propanediol.

The present invention provides a method of 1,3-propanediol production directly using crude glycerol, a by-product from biodiesel production, in which the crude glycerol, a by-product during the production of biodiesel, is further converted to 1,3-propanediol, and therefore the expenditure of glycerol isolation and purification is saved and the production cost is reduced effectively. The method can be used in the integrated production of biodiesel and 1,3-propanediol, in which both biodiesel and 1,3-propanediol are made from cheap raw materials. The utilization of raw materials and glycerol is increased and the production cost is reduced.

The present invention provides a method of 1,3-propanediol production using crude glycerol, a by-product from biodiesel production directly. Using the method of the present invention, the crude glycerol without any further treatment can be used directly to produce 1,3-propanediol. The crude glycerol is the by-product from biodiesel production with chemical method, biological method or supercritical method.

In one embodiment according to the present invention, a method of production of 1,3-propanediol is provided, characterized in that crude glycerol, a by-product from biodiesel production, is used as substrate. The method comprising the steps of:

(a) inoculating a 1,3-propanediol-producing bacterial strain in a seed medium containing crude glycerol, a by-product from biodiesel production, (b) adding the seed culture into the fermentation medium containing crude glycerol, a by-product from biodiesel production, and fermenting, and (c) isolating and purifying 1,3-propanediol.

THE DESCRIPTION OF THE FIGURE

FIG. 1 illustrates the scheme of the biodiesel production from vegetable oils and animal fats by transesterification.

DETAIL DESCRIPTION OF THE INVENTION

The present invention provides a method of 1,3-propanediol production using crude glycerol, a by-product from biodiesel production directly. According to the method of the present invention, the crude glycerol, a by-product from biodiesel production, can be directly used to produce 1,3-propanediol without any further treatment. The crude glycerol can be the by-product from biodiesel production using chemical method, biological method or supercritical method.

In one embodiment, the present invention provides a method of production of 1,3-propanediol, characterized in that crude glycerol, a by-product from the biodiesel production, is used as the substrate, the method comprising the steps of: (a) inoculating a 1,3-propanediol-producing bacterial strain in the seed medium containing crude glycerol, a by-product from biodiesel production, (b) adding the seed culture into the fermentation medium containing crude glycerol, a by-product from biodiesel production, and fermenting, and (c) isolating and purifying 1,3-propanediol.

In one embodiment, crude glycerol, a by-product from biodiesel production, is the crude glycerol, a by-product produced during the production of biodiesel.

In one embodiment, the 1,3-propanediol-producing strain can be selected from the group consisting of *Klebsiella pneumoniae, Clostridium butyricum* and *Clostridium pasteurianum*.

In one embodiment, the crude glycerol, a by-product from biodiesel production, without any further treatment, is directly used as the substrate during fed-batch fermentation.

In one embodiment, the 1,3-propanediol-producing bacterial strain is cultured at 30° C. to 37° C. for 16 to 20 hours.

In one embodiment, the glycerol contained in the fermentation medium is crude glycerol, a by-product from biodiesel production, in a concentration of 10 to 30 g/L.

In one embodiment, the pH in step (b) during the fermentation is maintained in a range of 6.8 to 8.0, preferably by alkaline solutions or ammonia of 3 to 4M.

In one embodiment, the fermentation in step (b) is carried out at 30° C. to 37° C., under anaerobic or aerobic conditions.

In one embodiment, the concentration of glycerol in the fermentation broth is maintained at 10 to 40 g/L by feeding crude glycerol or a mixture of the crude glycerol and glucose in step (b), preferably the concentration ratio of glycerol to glucose in the mixture is 5~10:1.

In one embodiment, 1,3-propanediol is isolated and purified by desalination, distillation and vacuum rectification.

In one embodiment, other by-products such as 2,3-butanediol, lactic acid, acetic acid, ethanol or succinic acid are obtained.

In a preferable embodiment, the present invention provides a method of 1,3-propanediol production directly using crude glycerol, a by-product during the fermentation of biodiesel production, characterized in that the crude glycerol is directly used as the fermentation substrate for producing 1,3-propanediol by fermentation and as the feeding substrate during fed-batch fermentation, comprising the following steps:

(a) inoculating a 1,3-propanediol-producing bacterial strain selected from the group consisting of common used *Klebsiella pneumoniae, Clostridium butyricum* and *Clostridium pasteurianum* in a seed medium containing crude glycerol and culturing, preferably at 30° C. to 37° C. for 16 to 20 hours;

(b) adding the seed culture into a fermentation medium containing crude glycerol and fermenting, preferably 30° C. to 37° C., under anaerobic or aerobic conditions; during a fed-batch fermentation, feeding crude glycerol or a mixture of the crude glycerol and glucose (the concentration ratio of glycerol to glucose is 5~10:1) and maintaining the concentration of the glycerol in the fermentation broth in a range of 10 to 40 g/L; and controlling pH in a range of 6.8 to 8.0, preferably with alkaline solutions or ammonia of 3 to 4M;

(c) after fermentation, isolating and purifying 1,3-propanediol by desalination, distillation and vacuum rectification, and meanwhile recovering other by-products such as 2,3-butanediol, lactic acid, acetic acid, ethanol or succinic acid.

The substrate in the above fermentation for producing 1,3-propanediol is crude glycerol, a by-product produced in the biodiesel production, using chemical method, biological method or supercritical method.

In the present invention, the crude glycerol is directly used without further treatment. Some portion of such crude glycerol is used as the fermentation substrate and the other is used as the feeding substrate during fed-batch fermentation.

The method according to the present invention is useful in the integrated production of biodiesel and 1,3-propanediol.

The advantages of the method according to the present invention lie in that the 1,3-propanediol is produced by crude glycerol, a by-product in the biodiesel production, and other widely used chemicals such as 2,3-butanediol, lactic acid, acetic acid, ethanol or succinic acid are generated as co-products during the fermentation. According to the method of the present invention, the cost for purification of glycerol is saved and the production cost of 1,3-propanediol is reduced efficiently. If the method is used in the integrated production of biodiesel and 1,3-propanediol, the utilization efficiency of the raw materials and the production efficiency of biodiesel will be improved, and the production cost will be reduced greatly.

DEFINITIONS

The term "biodiesel" as used herein refers to a renewable energy source which is made from vegetable oils, animal fats and waste oils.

The term "crude glycerol, a by-product from biodiesel production" as used herein refers to the unpurified glycerol, a by-product obtained during the biodiesel production.

EXAMPLES

The present invention will be further illustrated by the following examples. In the following examples, the glycerol is crude glycerol, a by-product produced during the biodiesel production. The yeast extract was purchased from Wenzhou Jinju Condiment Company. $K_2HPO_4$ was purchased from Changsha Yutai Industry Company. $KH_2PO_4$ was purchased from Changsha Gaosheng Techniqure Chemical Company. $MgSO_4$ was purchased from Tianjin Changhe Chemical Company. $(NH_4)_2SO_4$ was purchased from Sinopec Baling Branch Company. Anti-foamer was purchased from Chemical Plant of Zhejiang University. Glucose was purchased from Shijiazhuang Huaying UnionGlucose Company. Other reagents were purchased from VAS Chemical Company (China).

Example 1

(1) Substrate for fermentation and feeding during fed-batch fermentation: the crude glycerol, a by-product from biodiesel production.

(2) Strain: *Klebsiella pneumoniae* (ACCC10082), purchased from the Institute of Microbiology, Chinese Academy of Sciences.

(3) Medium:

| Medium Compositions | Seed medium (/l) | Fermentation medium (/l) | Trace elements solution | (mg/l) |
|---|---|---|---|---|
| Glycerol | 20 g | 10-30 g | $ZnCl_2$ | 70 |
| $K_2HPO_4 \cdot 3H_2O$ | 4.45 g | 2.225 g | $MnCl_2 \cdot 4H_2O$ | 100 |
| $(NH_4)_2SO_4$ | 2.0 g | 2.0 g | $H_3BO_3$ | 60 |
| $KH_2PO_4$ | 1.3 g | 0.65 g | $CoCl_2 \cdot 6H_2O$ | 200 |
| $MgSO_4 \cdot 7H_2O$ | 0.2 g | 0.2 g | $NiCl_2 \cdot 6H_2O$ | 25 |
| Yeast extract | 1.0 g | 1.5 g | $NiCl_2 \cdot H_2O$ | 27.64 |
| Trace elements solution | 2 ml | 2 ml | $Na_2MoO_4 \cdot 2H_2O$ | 35 |
| $CaCO_3$ | 2.0 g | | $CuCl_2 \cdot H_2O$ | 20 |
| antifoamer | | 0.1 ml | $CuSO_4 \cdot 5H_2O$ | 29.28 |
| | | | HCl (37%) | 0.9 ml |

(3) Culture:

A. Seed culture: *Klebsiella pneumoniae* was inoculated in the seed medium containing 20 g/L of crude glycerol, a by-product from biodiesel production (500 ml flask with 100 ml medium) and incubated at 30° C. and 150 rpm for 20 h under aerobic condition.

B. Fermentation: A 5 L fermentor (Biostat B, Germany) with 4 L working volume was used for fermentation at 37° C. KOH was used to maintain pH 6.8. Seed culture was inoculated in the fermentation medium containing 30 g/L of crude glycerol, a by-product from biodiesel production. During a fed-batch fermentation, glucose and crude glycerol, a by-product from biodiesel production, were fed, wherein the concentration ratio of glycerol to glucose was 8:1, and the flow rate was adjusted in order to maintain the concentration of glycerol in the fermentation broth at 30 g/L. The fermentation was performed under anaerobic condition with 0.2 vvm Nitrogen aerated.

(4) Results:

After fermentation, the concentration of 1,3-propanediol in the fermentation broth reached 44 g/l. The molar yield of 1,3-propanediol was 0.45 and the productivity was 0.8 g/l/h. (The measurement methods of the fermentation products were described at Liu, Dehua et al., Substrate inhibition in fermentation of 1,3-propanediol and countermeasures to it, Modern Chemical Industry, 2002 (7): 34-38)

Example 2

(1) Substrate for fermentation and feeding during fed-batch fermentation: the crude glycerol, a by-product from biodiesel production.

(2) The strains and the media were same as those in example 1.

(3) Culture:

A. Seed culture: *Klebsiella pneumoniae* was inoculated in the seed medium containing 20 g/L of crude glycerol, a by-product from biodiesel production, (500 ml flask with 100 ml medium) and incubated at 37° C. and 150 rpm for 16 h under aerobic condition.

B. Fermentation: A 5 L fermentor with 4 L working volume was used for fermentation at 37° C. KOH was used to maintain pH 8.0. Seed solution was inoculated in the fermentation medium containing 30 g/L of crude glycerol, a by-product from the biodiesel production. During a fed-batch fermentation, glucose and crude glycerol, a by-product from biodiesel production were fed, wherein the concentration ratio of glycerol to glucose was 10:1 and the feeding rate was adjusted in order to maintain the concentration of glycerol in the fermentation broth at 30 g/L. During the first 32 hours of the fermentation, the fermentation was performed under anaerobic condition with 0.2 vvm Nitrogen aerated. After 32 h, the fermentation was performed under aerobic condition with 0.2 vvm air aerated.

(4) Results:

After fermentation, the concentration of 1,3-propanediol in the fermentation broth was 64 g/l. The molar yield of 1,3-propanediol was 0.51 and the productivity was 0.95 g/l/h.

Example 3

(1) Substrate for fermentation and feeding during fed-batch fermentation: the crude glycerol, a by-product from biodiesel production.

(2) The strains and the media were same as those in example 1.

(3) Culture:

A. Seed culture: *Klebsiella pneumoniae* was inoculated in the seed medium containing 20 g/L of crude glycerol, a by-product from biodiesel production (500 ml flask with 100 ml solution) and incubated at 30° C. and 150 rpm for 16 h under aerobic undition.

B. Fermentation: A 50 L fermentor (Biostat B, Germany) with 40 L working volume was used for fermentation at 37° C. KOH was used to maintain pH 7.0. Seed solution was inoculated to the fermentation medium containing 10 g/L of crude glycerol, a by-product from biodiesel production. During a fed-batch fermentation, glucose and crude glycerol, a by-product from biodiesel production, were fed, wherein the concentration ratio of glycerol to glucose was 10:1 and the feeding rate was controlled in order to maintain the concentration of glycerol in the fermentation broth at 10 g/L at first 10-16 hours and at 30 g/L after 16 h. During the fermentation, 0.5 vvm air was aerated.

(4) Results:

After fermentation, the concentration of 1,3-propanediol in the fermentation broth was 67 g/l. The molar yield of 1,3-propanediol was 0.59 and the productivity was 1 g/l/h.

Example 4

(1) Substrate for fermentation and feeding during fed-batch fermentation: the crude glycerol, a by-product during the biodiesel production.

(2) The strains and the media were same as those in example 1.

(3) Culture:

A. Seed culture: *Klebsiella pneumoniae* was inoculated in the seed medium containing 20 g/L of crude glycerol, a by-product from biodiesel production (500 ml flask with 100 ml solution) and incubated at 30° C. and 150 rpm for 16 h under aerobic condition.

B. Fermentation: A 500 L fermentor with 350 L working volume was used for fermentation 37° C. KOH was used to maintain pH 7.0. Seed culture was inoculated to the fermentation medium containing 20 g/L of crude glycerol, a by-product from biodiesel production. During a fed-batch fermentation, glucose and crude glycerol, a by-product from biodiesel production, were fed, wherein the concentration ratio of glycerol to glucose was 10:1 and the feeding rate was controlled in order to maintain the concentration of glycerol in the fermentation broth at 10 g/L at first 10-16 hours and at 30 g/L after 16 h. During the fermentation, 0.5 vvm air was aerated.

(4) Results:

After fermentation, the concentration of 1,3-propanediol in the fermentation broth was 63.2 g/l. The molar yield of 1,3-propanediol is 0.60 and the productivity was 1.1 g/l/h.

We claimed:

1. A method of 1,3-propanediol production using crude glycerol, a by-product from biodiesel production, comprising:
   (a) inoculating a 1,3-propanediol-producing bacterial strain of *Klebsiella pneumoniae* in a seed culture medium containing the crude glycerol,
   (b) adding the resultant seed culture to a fermentation medium containing the crude glycerol, and fermenting under aerobic conditions at 30° C. to 37° C. to produce 1,3-propanediol, wherein a mixture of the crude glycerol and glucose is fed into the fermentation medium and the concentration of the glycerol in the fermentation medium is maintained at 10 to 40 g/L, wherein the crude glycerol from biodiesel production is added to the media in step (a) and in step (b) without any pretreatment, and
   (c) isolating and purifying 1,3-propanediol from fermentation medium.

2. The method according to claim 1, wherein in step (a) the bacterial strain is cultured at 30° C. to 37° C. for 16 to 20 hours.

3. The method according to claim 1, wherein the fermentation medium in step (b) contains 10 to 30 g/L of crude glycerol.

4. The method according to claim 1, wherein the pH during the fermentation in step (b) is kept in a range of 6.8 to 8.0.

5. The method according to claim 4, wherein the pH is maintained by using a 3 to 4 M of alkaline solution or ammonia.

6. The method according to claim 1, wherein the concentration ratio of the glycerol to glucose in the mixture is 5:1 to 10:1.

7. The method according to claim 1, wherein the 1,3-propanediol is isolated and purified by desalination, distillation and vacuum rectification.

8. The method according to claim 1, wherein co-products 2,3-butanediol, lactic acid, acetic acid, ethanol or succinic acid are produced.

9. The method according to claim 1, wherein a mixture of crude glycerol and glucose without any further treatment, is fed as feeding substrate during fed-batch fermentation.

10. The method according to claim 1, wherein biodiesel is produced by a chemical method, a biological method or a supercritical method, and the crude glycerol is not further treated.

11. The method according to claim 1, wherein the crude glycerol a by-product from biodiesel production is used as the substrate for the fermentation production of 1,3-propanediol, comprising:
    (a) inoculating a strain of *Klebsiella pneumoniae*, into the seed medium containing the crude glycerol and incubating at 30° C. to 37° C. for 16 h to 20 h,
    (b) adding the seed culture to a fermentation medium containing the crude glycerol and incubating at 30° C. to 37° C. under aerobic conditions to produce 1,3-propanediol, wherein the mixture of the crude glycerol and glucose is fed and the concentration of glycerol in the fermentation medium is maintained at 10 to 40 g/L, wherein the concentration ratio of glycerol to glucose in the mixture is 5 to 10:1, and alkaline solutions or ammonia of 3 to 4M are used to maintain pH in a range of 6.8 to 8.0 wherein the crude glycerol from biodiesel production is added to the media in step (a) and in step (b) without any pretreatment,
    (c) after fermentation, isolating and purifying 1,3-propanediol from fermentation medium by desalination, distillation and vacuum rectification.

12. The method according to claim 11, wherein a mixture of crude glycerol and glucose is fed as feeding substrate during fed-batch fermentation in order to maintain the concentration of glycerol in the fermentation broth at 30 g/L.

13. The method according to claim 11, wherein the biodiesel is produced by a chemical method, a biological method or a supercritical method.

* * * * *